(12) United States Patent
Pickering et al.

(10) Patent No.: US 8,962,676 B2
(45) Date of Patent: Feb. 24, 2015

(54) CAUSAL THERAPY OF DISEASES OR CONDITIONS ASSOCIATED WITH CNS OR PNS DEMYELINATION

(75) Inventors: Mark Pickering, Dublin (IE); Keith Murphy, Dublin (IE)

(73) Assignee: University College Dublin, National University of Ireland, Dublin, Dublin (IE)

( * ) Notice: Subject to any disclaimer, the term of this patent is extended or adjusted under 35 U.S.C. 154(b) by 72 days.

(21) Appl. No.: 13/503,105

(22) PCT Filed: Oct. 22, 2010

(86) PCT No.: PCT/EP2010/065961
§ 371 (c)(1),
(2), (4) Date: Jul. 12, 2012

(87) PCT Pub. No.: WO2011/048208
PCT Pub. Date: Apr. 28, 2011

(65) Prior Publication Data
US 2012/0269762 A1    Oct. 25, 2012

Related U.S. Application Data

(60) Provisional application No. 61/253,985, filed on Oct. 22, 2009.

(51) Int. Cl.
*A61K 31/4025* (2006.01)
(52) U.S. Cl.
CPC ................... *A61K 31/4025* (2013.01)
USPC .... 514/424; 424/78.37; 424/85.6; 424/133.1; 514/326
(58) Field of Classification Search
CPC .... C07D 207/26; C07D 207/12; A61K 31/40; A61K 31/4025
USPC ............ 424/78.37, 133.1, 85.6; 514/326, 424
See application file for complete search history.

(56) References Cited

U.S. PATENT DOCUMENTS
4,620,973 A    11/1986    Truog

FOREIGN PATENT DOCUMENTS
EP    1 356 812    10/2003

OTHER PUBLICATIONS

Rashid et al. The Journal of Pharmacology and Experimental Therapeutics. vol. 303, No. 1.*

(Continued)

*Primary Examiner* — Savitha Rao
*Assistant Examiner* — Angela Brown-Pettigrew
(74) *Attorney, Agent, or Firm* — Nixon Peabody LLP

(57) ABSTRACT

The present invention is directed to the treatment of demyelination as an underlying cause of the disease of multiple sclerosis (MS) in a mammal, the method comprising promoting remyelination of myelination of axonal cells by administering to the mammal a 2-oxopyrrolidine compound having a general formula I:

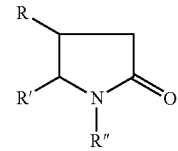

wherein R=R'=H, and R''=$CH_2CONH$-$(2,6CH_3)C_6H_3$ or a pharmaceutically acceptable salt thereof.

4 Claims, 4 Drawing Sheets

(56) References Cited

OTHER PUBLICATIONS

Pöllmann et al. CNS Drugs. 2000 22(4) 291-324.*
Paul Gilbert, The Unknown Disease: Multiple Sclerosis, 2007.*
Rashid et al. The Journal of Pharmacology and Experimental Therapeutics. vol. 303, No. 1, 2002.*
Eggenberger et al., Neuro-Ophthalmology, 30(4):105-108 (2006). "Levetiracetam effect in demyelinating ocular flutter with myoclonus."
Feys et al., Multiple Sclerosis, 15(3):371-378 (2009). "The effect of levetiracetam on tremor severity and functionality in patients with multiple sclerosis."
Groom et al., Annals of the New York Academy of Sciences, 993:229-275 (2003). "Multiple sclerosis and glutamate."
Hawker et al., Archives of Neurology, 60(12):1772-1774 (2003). "Levetiracetam for phasic spasticity in multiple sclerosis."
Onishchenko et al., Neuroscience and Behavioral Physiology, 38(1):49-54 (2008). "Changes at the focus of experimental ischemic stroke treated with neuroprotective agents."
Striano et al., Journal of Neurology, 253(6):762-766 (2006). "Levetiracetam for cerebellar tremor in multiple sclerosis; an open-label pilot tolerability and efficacy study."

\* cited by examiner

CAUSAL THERAPY OF DISEASES OR CONDITIONS ASSOCIATED WITH CNS OR PNS DEMYELINATION

CROSS REFERENCE TO RELATED APPLICATIONS

This application is a 35 U.S.C. §371 National Phase Entry Application of International Application No. PCT/EP2010/065961 filed Oct. 22, 2010, which designates the U.S., and which claims benefit under 35 U.S.C. §119(e) of U.S. Provisional Application No. 61/253,985, filed Oct. 22, 2009, the contents of which are incorporated herein by reference in their entireties.

TECHNICAL FIELD

The invention relates to the treatment of diseases or conditions associated with central or peripheral nervous system demyelination in human subject. In particular, the invention relates to a causal therapy of multiple sclerosis (MS).

BACKGROUND TO THE INVENTION

Multiple Sclerosis (MS) is an autoimmune disease which occurs when T lymphocytes invade the CNS and damage the oligodendrocytes responsible for the maintenance of axonal myelin sheaths, resulting in impaired neuronal activity. The disease is characterised symptomatically by varying degrees of visual, motor, sensory and cognitive dysfunction. MS is broadly classified into four categories, defined by the progress pattern of the disease (Lublin and Reingold, 1996). For most patients, the disease begins as relapsing-remitting MS, characterised by periods of spontaneous remission between symptomatic relapses. This often progresses to a form where remissions cease, resulting in continuous neurological decline, a type classified as secondary progressive MS. In cases where no remission occurs after the onset of the disease and subsequent worsening of neurological symptoms the disease is classified as primary progressive MS. The final category, progressive-relapsing MS, is the rarest subtype, and is characterised by a steady increase in severity of the neurological impairments, with superimposed acute attacks of greater severity.

Although there is some evidence for genetic factors increasing the risk of MS (Sadovnick, 1996), the "trigger" which causes the disease is unknown and occurrence cannot be predicted, eliminating the possibility of preventative strategies being developed in the foreseeable future. The prevalence rate of MS has been estimated at approximately 1 in 700, affecting females at approximately twice the rate of males, although prevalence estimates vary greatly depending on region (Rosait, 2001). As a progressive disease with considerable resultant disability, the condition is associated with a high cost of illness, a significant proportion of which relates to drug costs. In the US in 2004, 98.1% of all MS patients used medicines at a mean cost of $18,628 per patient per year, of which $16,050 was the cost of disease modifying drugs (Kobelt et al, 2005). In Europe, cost of drug treatment is highest at the earliest stage of disease, and varies between countries, from € 4,324 per patient per year in the UK to € 12,881 in Germany (Kobelt et al, 2006). Despite this significant expenditure on treatment, current pharmaceutical therapies, all of which target the immune system's role in the disease, are limited to slowing the progress of the disease or decreasing the rate of disease recurrence, and are largely ineffective in the treatment of progressive disease forms.

2-oxopyrrolidine compounds are known to effect cerebral function (Japanese Patent Application Publication No: 56.2960/1981). In particular, it has been suggested in the literature that NEFIRACETAM (N-(2,6-dimethylphenyl)-2-(2-oxo-1-pyrrolidinyl)acetamide) may improve cerebral function and cognition (Moriguchi et al. 2009, Moriguchi et al. 2008), improve intellectual ability following stroke (US Patent Application No:2002/0055534), and have anticonvulsant and neuroprotective effects in animal models (Kitano et al. 2005).

It is an object of the invention to overcome at least one of the above problems.

Statements of Invention

Figure 1A:
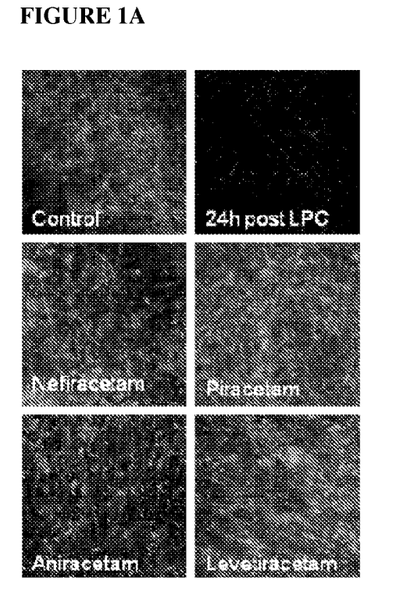
Figure 1B:
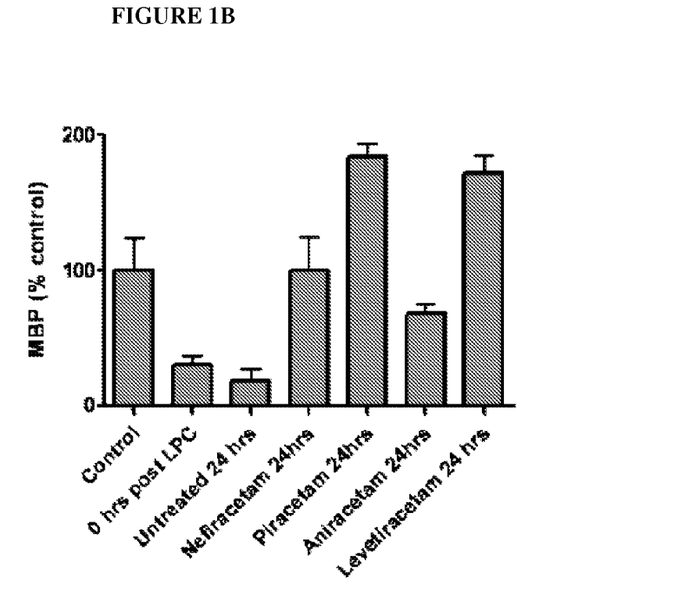
Figure 2A:
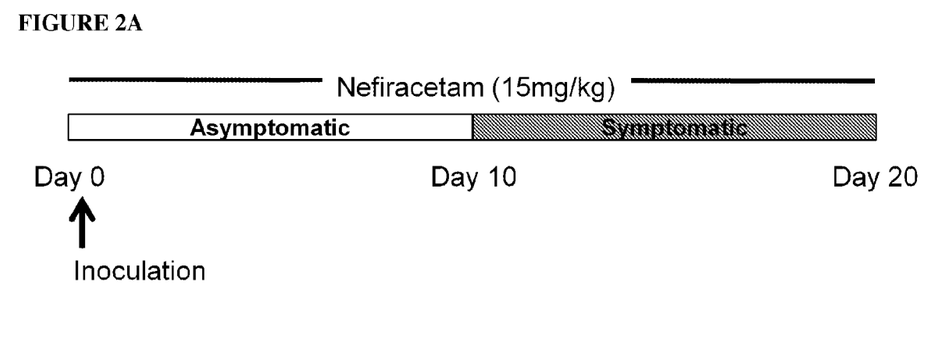
Figure 2B:
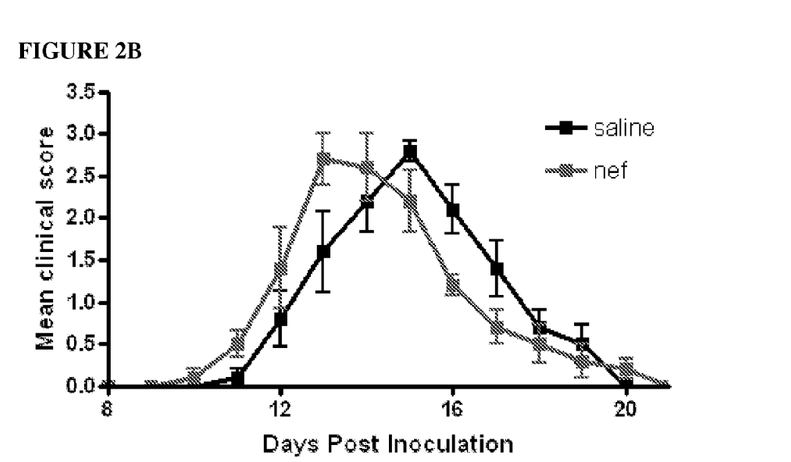
Figure 3A:
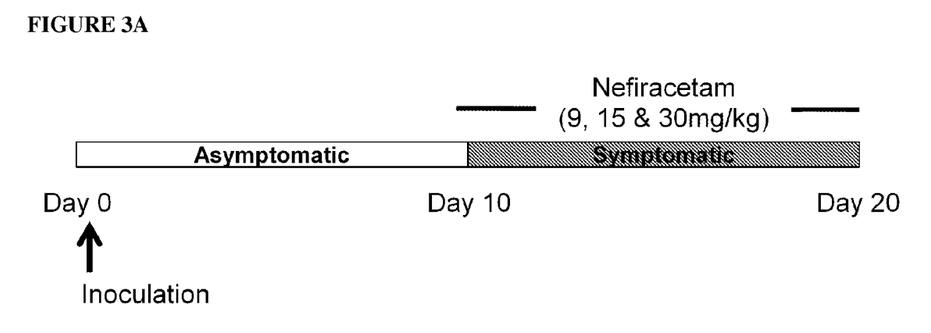
Figure 3B:
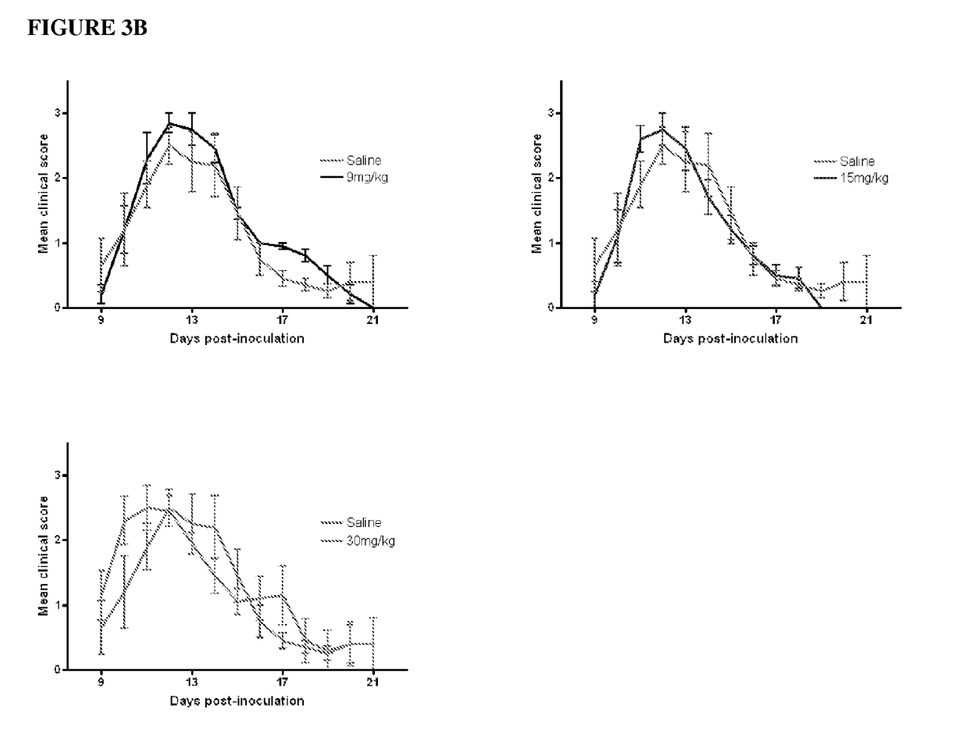
Figure 4A:
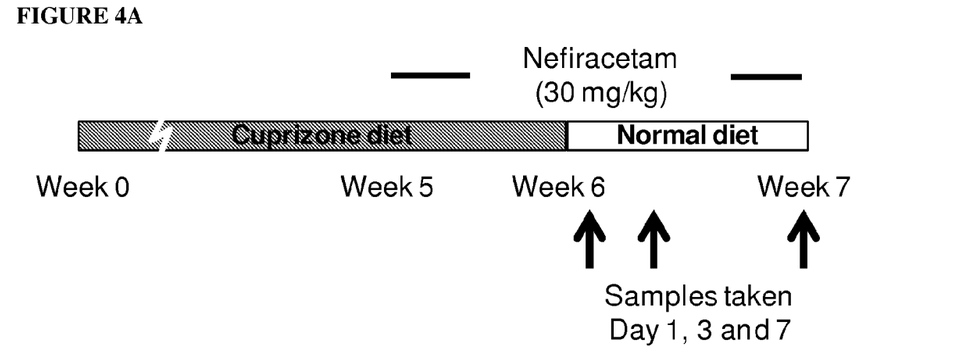
Figure 4B:
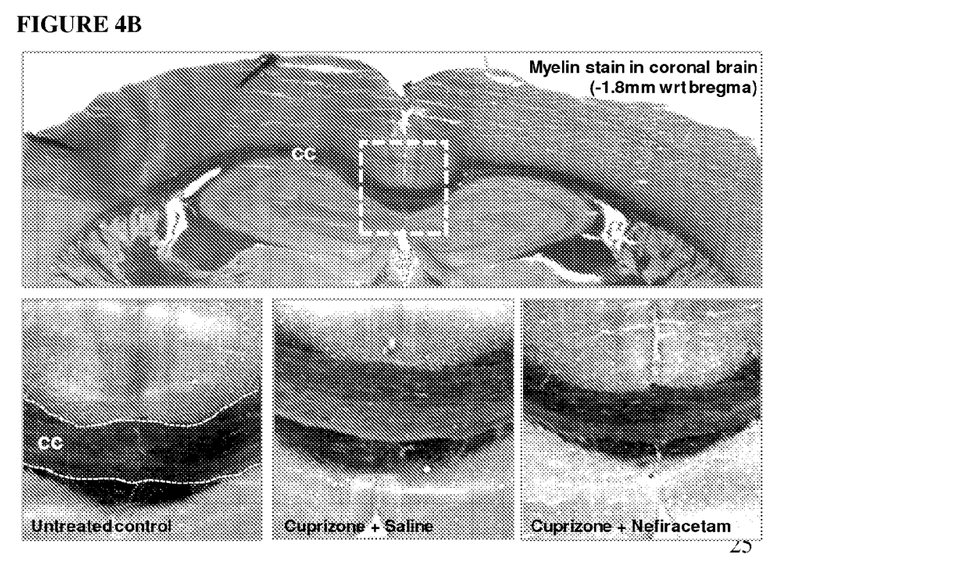
Figure 4C:
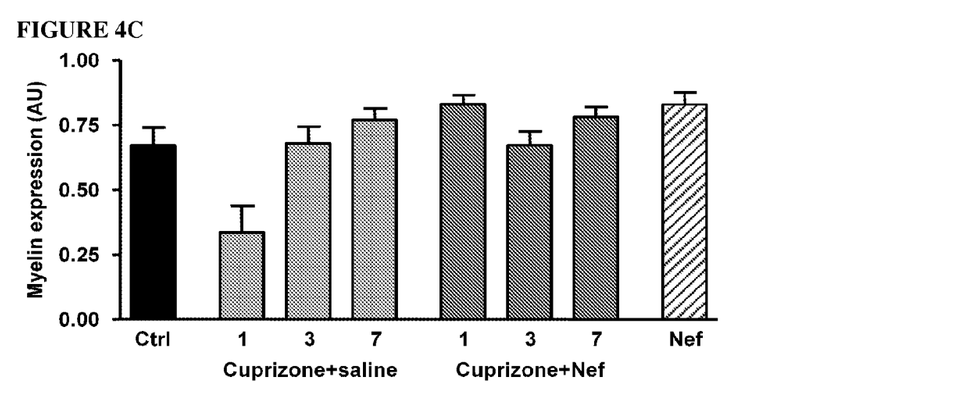

The invention is based on the surprising finding that 2-oxopyrrolidine compounds (hereafter "Active") are capable of maintaining the integrity (for example, preventing demyelination and/or promoting remyelination) of axonal myelin sheaths in cell and animal models of diseases associated with CNS or PNS demyelination. Data is provided below which clearly shows that the Active accelerates myelin repair in axonal cells that have been damaged in a cuprizone animal model of demyelination, and restores myelin expression following 6 days of treatment (See FIGS. 4A to 4C). Data is also provided which shows the effects of the Active is a non-immune mediated effect (See FIGS. 2 and 3) and that the effects are achieved using four different species of the 2-oxopyrrolidine class of compounds (See FIG. 1). Thus, the invention broadly relates to the use of the Active in the causal treatment of a disease caused by axonal demyelination, in which the Active maintains the integrity of myelination (for example by promoting remyelination, and/or preventing demyelination, of the axonal sheaths). The invention is particularly directed to the causal treatment of CNS demyelination diseases, for example MS, especially primary progressive MS and/or relapse remitting MS, and PNS demyelination diseases, for example Charcot-Marie-Tooth Disease. The Active of the invention may be suitably administered when a patient is in relapse (i.e. upon relapse), and be continued while the patient is in relapse, with a view to attenuating the severity of the relapse, and/or accelerating disease remission. Alternatively, the Active may be administered continuously with a view to prolonging the remission period, and/or attenuating the severity of the relapse, and/or preventing relapse. The invention also relates to the use of the Active as a treatment for symptoms of demyelination disease, especially MS, selected from vision deficits, motor control deficits, and sensation deficits.

Accordingly, the invention broadly relates to an Active for use in the causal treatment or prevention of a disease or condition associated with central nervous system (CNS) or peripheral nervous system (PNS) demyelination in a mammal by maintaining the integrity of myelination of axonal cells.

In this specification, the term "maintaining the integrity of myelination of axonal cells" should be understood to mean effecting remyelination of axonal cells, inhibiting or preventing demyelination of axonal cells, or both. The term "causal" treatment should be understood to mean a treatment of demyelination as an underlying cause of the disease, and to exclude treatments that are intended to directly address clinical symptoms of the disease (symptomatic treatment).

In another aspect, the invention broadly relates to a method for the treatment or prevention of a disease or condition associated with central nervous system (CNS) or peripheral nervous system (PNS) demyelination in a mammal by maintaining the integrity of myelination of axonal cells, the method comprising a step of administering a clinically effective amount of an Active to an individual in need thereof.

In another aspect, the invention relates to a method for treating a relapse, especially an acute relapse, of a disease or condition associated with central nervous system (CNS) or peripheral nervous system (PNS) demyelination in a mammal by maintaining the integrity of myelination of axonal cells., the method comprising the step of administering a clinically effective amount of an Active to the mammal upon relapse of the disease or condition. Preferably, the administration of the clinically effective amount of the Active is continued during a period of relapse of the disease or condition and is preferably discontinued upon remission of the disease or condition.

In another aspect, the invention relates to a method of prolonging a period of remission of a disease or condition associated with central nervous system (CNS) or peripheral nervous system (PNS) demyelination in a mammal by maintaining the integrity of myelination of axonal cells, the method comprising the step of administering a clinically effective amount of an Active to the mammal during a period of remission of the disease or condition. Preferably, the administration of the clinically effective amount of the Active is continued during a period of relapse of the disease or condition.

In another aspect, the invention relates to a non-immune mediated therapy (preferably a non-immune mediated causal therapy) for a disease or condition associated with central nervous system (CNS) or peripheral nervous system (PNS) demyelination in a mammal, especially multiple sclerosis (MS), especially primary progressive MS, the method comprising a step of administering a clinically effective amount of an Active to the mammal in an amount sufficient to result in a clinically significant remyelination, or inhibition of demyelination, of axonal sheaths in the mammal. The term "non-immune mediated therapy" should be understood to mean a therapy which is not directed at dampening down of the immune response in the mammal.

In one embodiment, the methods and uses of the invention comprise a combination therapy or use comprising the administration of an Active in parallel with administration of an immune mediated therapeutic. The term "immune mediated therapeutic" or "immunosuppressant" are used interchangeably and should be understood to mean a causal therapeutic that is aimed at modulating the immune response in a mammal to prevent, inhibit or ameliorate demyelination of axonal sheaths of CNS or PNS neuronal cells. Examples of immune mediated therapeutics or immunosuppressants are well known in the field, and include Natalizumab or TYSABRI (Elan), Interferon beta 1b (BETASERON), Interferon beta 1a (AVONEX), glatiramer acetate or COPAXONE (Teva), and daclizumab (ZENEMAX). The Active may be administered at the same time as the immune mediated therapeutic, or the two medicaments may be administered in a staggered manner. In one embodiment, the Active and immune mediated therapeutic are provided in a single unit dose form, for example, a liquid or tablet or the like.

Thus, in a further embodiment, the invention relates to a combination therapy for a disease or condition associated with central nervous system (CNS) or peripheral nervous system (PNS) demyelination in a mammal, for example multiple sclerosis, the method comprising a step of treating the mammal with (a) an immune mediated therapeutic to dampen or suppress an immune mediated response in the mammal in tandem with (b) an Active to promote remyelination of CNS or PNS neurons.

In one aspect, the invention relates to a method for the causal treatment of diseases or conditions associated with CNS or PNS demyelination in a human subject by inhibiting, ameliorating or reversing demyelination of CNS or PNS neuronal cells, the method comprising the steps of administering to the subject an amount of the Active effective to cause a clinically significant level of inhibition, amelioration, or reversal of demyelination of a CNS or PNS neuronal cells.

In another aspect, the invention relates to a method for inhibiting, ameliorating or reversing demyelination of CNS or PNS cells in a human subject in need thereof, the method comprising the steps of administering to the subject an amount of the Active effective to inhibit, ameliorate, or reverse demyelination of a CNS or PNS neuronal cells.

In another aspect, the invention relates to a method for preventing, or slowing the progression of diseases or conditions associated with CNS or PNS demyelination in a human subject by inhibiting, ameliorating or reversing demyelination of CNS or PNS cells, the method comprising the steps of administering to the subject an amount of the Active effective to inhibit, ameliorate, or reverse demyelination of a CNS or PNS neuronal cells.

In another aspect, the invention relates to a method for the treatment of one or more symptoms of a disease or condition associated with CNS or PNS demyelination in a human subject, the method comprising the steps of administering to the subject an amount of the Active effective to inhibit, ameliorate, or reverse demyelination of a CNS or PNS cell type. The symptoms are typically selected from the group consisting of vision deficits, motor control deficits, sensation deficits, and cognitive function deficits. In a preferred embodiment, the symptoms are selected from vision, motor control, and sensation, deficits.

In a preferred embodiment of the invention, the Active is NEFIRACETAM.

In a preferred embodiment of the invention, the condition associated with CNS or PNS demyelination is MS.

Thus, in a particularly preferred embodiment, the invention relates to a method for treating one or more symptoms of MS in a mammal selected from vision deficits, sensation deficits, and motor control deficits by promoting remyelination and/or inhibiting demyelination of axonal myelin sheaths, the method comprising the step of administering to the subject a clinically effective amount of an Active.

In a further particularly preferred embodiment, the invention relates to a method for treating primary progressive MS in a human subject, especially symptomatic treatment of vision deficits, sensation deficits, and/or motor control deficits, and optionally cognitive function deficits, the method comprising the step of administering to the subject an amount of NEFIRACETAM effective to inhibit, ameliorate or reverse demyelination of axonal cells in the CNS.

In a further particularly preferred embodiment, the invention relates to a method for treating one or more symptoms of primary progressive MS in a human subject selected from vision deficits, sensation deficits, and motor control deficits, and optionally cognitive function deficits, the method comprising the step of administering to the subject an amount of NEFIRACETAM effective to inhibit, ameliorate or reverse demyelination of axonal cells in the CNS.

The invention also relates to a pharmaceutical formulation comprising a combination therapy of an immune mediated therapeutic of the type capable of reducing the length and/or degree of inflammation-mediated damage to insulating cells around nerve fibres, and an Active. Such a formulation would be especially suitable for causal or symptomatic treatment, or prevention of autoimmune demyelinating diseases or conditions.

In this specification, the term clinically effective amount" should be taken to mean an amount of Active which results in a clinically significant inhibition, amelioration or reversal of demyelination, or clinically significant remyelination, of CNS or PNS neuronal cells. Details of dosages of NEFIRACETAM that are readily tolerated and readily orally administered are described in the literature (Robinson et al. 2009). Suitably, the Active is administered at a dose of between 1 microgram and 50 milligrams daily, preferably between 1 milligram and 40 milligrams daily, more preferably between 5 milligrams and 40 milligrams daily.

2-oxopyrrolidine compounds (the "Active") are described in Japanese Patent Application Publication No: 56.2960/1981 and in International Patent Application Publication No: WO2006113937, the contents of which are incorporated herein by reference. Thus, in this specification, the term "2-oxopyrrolidine compound" or "Active" refers to a compound of general formula I:

wherein R is hydrogen, hydroxyl or aminomethyl;
R' is hydrogen or piperidinocarbonyl group;
R" is hydrogen, aminocarbonylalkyl optionally N-substituted with a di($C_1$-$C_4$)alkylamino-($C_2$-$C_4$)alkyl group, anilinocarbonylalky optionally mono or disubstituted on the benzene ring with methyl, methoxy, or halogen; benzyl, optionally mono or disubstituted on the benzene ring with methyl, methoxy, or halogen;
wherein one or two of R, R' and R" is hydrogen;
with the provisos that when R' is other than hydrogen, then R and R" are both hydrogen, and
when R is other then hydrogen, then R' is hydrogen, or a pharmaceutically acceptable salt thereof.

Examples of 2-oxopyrrolidine compound of general Formula (I) useful for the present invention are:

Piracetam: wherein R=R'=H, R"=$CH_2$ $CONH_2$ (aminocarbonylmethyl);
Aniracetam: wherein R=R'=H, R"=$CH_2$ $C_6H_4$-$pOCH_3$ (4-methoxybenzyl);
Oxiracetam: wherein R=OH, R'=H; R"=$CH_2$ $CONH_2$;
Pramiracetam: wherein R=R'=H, R"=$CH_2$ $CONHCH_2$ $CH_2$ $N[CH(CH_3)_2]_2$, (2-disisopropylaminoethyl)aminocarbonylmethyl;
Nefiracetam: wherein R=R'=H, R"=$CH_2$ CONH-(2, $6CH_3$)$C_6H_3$ (anilinocarbonylmethyl);
Nebracetam: wherein R=$CH_2$ $NH_2$ (aminomethyl), R'=H; R"=$CH_2$ $C_6H_5$ (benzyl);
Fasoracetam: wherein R=R"=H, R'=piperidinocarbonyl;
Fasoracetam: wherein R=R"=H, R'=piperidinocarbonyl (see below);

Levetiracetam, wherein R=R'=H; R"=1-aminocarbonylpropyl (see below).

Other racetams included within the scope of the invention include Phenylpiracetam (Carphedon), Etiracetam, Nicoracetam (racetam structure bonded to niacin), Rolziracetam, Nebracetam, Imuracetam, Coluracetam (potential use in prevention and treatment of ischemic retinopathy and retinal and optic nerve injury), Dimiracetam, Brivaracetam, and Seletracetam.

In a preferred embodiment, the Active is selected from the group consisting of: PIRACETAM, ANIRACETAM, PRAMIRACETAM, NEBRACETAM, FASORACETAM, LEVETIRACETAM and OXIRACETAM. Ideally, the Active is selected from the group consisting of PIRACETAM, ANIRACETAM, LEVETIRACETAM and NEFIRACETAM. Ideally, the Active is NEFIRACETAM (N-(2,6-dimethylphenyl)-2-(2-oxo-1-pyrrolidinyl)acetamide).

The term "diseases or conditions associated with CNS or PNS demyelination" should be understood to mean a pathology in which axonal demyelination of a CNS or PNS neuronal cell types is an underlying cause of the symptoms of the pathology. Examples of these diseases/conditions include demyelinating diseases of the central nervous system such as:

Multiple sclerosis including relapse remitting MS (RRMS), primary progressive MS, secondary progressive MS, and progressive relapsing MS; Idiopathic inflammatory demyelinating diseases; Transverse myelitis; Devic's disease; Progressive multifocal leukoencephalopathy; Optic neuritis; and Leukodystrophies, and demyelinating diseases of the peripheral nervous system such as: Guillain-Barré syndrome and its chronic counterpart, chronic inflammatory demyelinating polyneuropathy; anti-MAG peripheral neuropathy; Charcot-Marie-Tooth Disease; and Vitamin B12 deficiency (change->B12 deficiency causes subacute combined degeneration of the spinal cord . . . spinal cord is part of the CNS, disease is "combined" b/c of demyelination of the Dorsal Columns—decreased vibration and proprioception sensation—and Corticospinal Tract—upper motor neuron disease symptoms).

In one embodiment, the disease or condition is one associated with CNS demyelination. In another embodiment, the disease or conditions is associated with PNS demyelination.

In this specification, the term administering should be taken to include any form of delivery that is capable of delivering the Active to the CNS or PNS, including intravenous delivery, oral delivery, intramuscular delivery, intrathecal delivery, and inhaled delivery. Methods for achieving these means of delivery will be well known to those skilled in the art of drug delivery, and include:

Delivered intrathecally by mini-osmotic pump. (ref: Ignacio et al., Ann. N.Y. Acad. Sci. 2005, 1053: 121-136).

Intramuscular delivery directly into muscle(s) by syringe or mini osmotic pump (Azzouz et al., Nat. Med. 2005; 11(4):429-33).

Intraperitoneal—for systemic administration—directly administered to peritoneum by syringe or mini osmotic pump (Kieran et al., Nat Med 2004; 10(4):402).

Subcutaneous—for systemic administration—directly administered below the skin by syringe (Reinholz et al., Exp Neurol. 1999; 159(1):204-16).

Intraventricular—direct administration to the ventricles in the brain, by injection or using small catheter attached to an osmotic pump. (Sathasivam et al., 2005 Neuropath App Neurobiol; 31(5): 467)

Implant—can be prepared in an implant (eg small silicon implant) that will release Active.

Implant can be placed at muscles or directly onto the spinal cord (Kieran and Greensmith, 2004 Neurosci 125(2): 427-39).

Additionally, administration of an Active to humans and animals is described in the following publications:

Feys P, D' hooghe M B, Nagels G, Helsen W F. The effect of levetiracetam on tremor severity and functionality in patients with multiple sclerosis. Mult Scler. 2009 March; 15(3):371-8. Epub 2009 Jan. 23. PubMed PMID: 19168602.

Groom A J, Smith T, Turski L. Multiple sclerosis and glutamate. Ann N Y Acad. Sci. 2003 May; 993:229-75; discussion 287-8.

Gusev E I, Boĭko A N, Kol'iak E V, Karalkin A V, Kamchatov P R, Martynov M Iu. [The impact of microcirculation dysfunction on the clinical presentations of multiple sclerosis in patients above 45 years and the possible ways of correction of the vascular pathology]. Zh Nevrol Psikhiatr Im S S Korsakova. 2008; 108(5):25-31. Russian. PubMed PMID: 18577954.

Hawker K, Frohman E, Racke M. Levetiracetam for phasic spasticity in multiple sclerosis. Arch Neurol. 2003 December; 60(12):1772-4. PubMed PMID: 14676055.

Le D T, Shin C, Jackson-Friedman C, Lyden P D. (2001) Quantitative effects of nefiracetam on spatial learning of rats after cerebral embolism. J Stroke Cerebrovasc Dis. 10:99-105.

Mula M, Sander J W. Negative effects of antiepileptic drugs on mood in patients with epilepsy. Drug Saf. 2007; 30(7):555-67. Review. PubMed PMID: 17604407.

Murphy K J, Foley A G, O'connell A W, Regan C M. (2006) Chronic exposure of rats to cognition enhancing drugs produces a neuroplastic response identical to that obtained by complex environment rearing. Neuropsychopharmacology. 31:90-100

Papacostas S S, Papathanasiou E S, Myrianthopoulou P, Stylianidou G. Tuberous sclerosis successfully treated with levetiracetam monotherapy: 18 months of follow-up. Pharm World Sci. 2007 August; 29(4):350-2. Epub 2007 Mar. 1. PubMed PMID: 17333500.

Rossi S, Mataluni G, Codecà C, Fiore S, Buttari F, Musella A, Castelli M, Bernardi G, Centonze D. Effects of levetiracetam on chronic pain in multiple sclerosis: results of a pilot, randomized, placebo-controlled study. Eur J Neurol. 2009 March; 16(3):360-6. PubMed PMID: 19364364.

Solaro C, Brichetto G, Capello E, Abuarqub S, Sanguineti V. Activity, tolerability and efficacy of levetiracetam on cerebellar symptoms in multiple sclerosis patients: a pilot kinematic study. Eur J Neurol. 2008 June; 15(6): 619-26. PubMed PMID: 18474077.

Striano P, Coppola A, Vacca G, Zara F, Brescia Morra V, Orefice G, Striano S. Levetiracetam for cerebellar tremor in multiple sclerosis: an open-label pilot tolerability and efficacy study. J Neurol. 2006 June; 253(6): 762-6. Epub 2006 May 12. PubMed PMID: 16683063.

Takeo S, Niimura M, Miyake-Takagi K, Nagakura A, Fukatsu T, Ando T, Takagi N, Tanonaka K, Hara J (2003) A possible mechanism for improvement by a cognition-enhancer nefiracetam of spatial memory function and cAMP-mediated signal transduction system in sustained cerebral ischaemia in rats. Br J. Pharmacol. 138:642-54

Ueda M, Fujita R, Koji T, Ueda H. (2004) The cognition-enhancer nefiracetam inhibits both necrosis and apoptosis in retinal ischemic models in vitro and in vivo. J Pharmacol Exp Ther. 309:200-7.

Zhao X, Yeh J Z, Narahashi T. Post-stroke dementia. (2001) Nootropic drug modulation of neuronal nicotinic acetylcholine receptors. Ann N Y Acad. Sci. 939:179-86

US2001/0041734 A1 Method of treating traumatic brain injury and other neuronal disorders US2002/0055534 A1 Method for treating neurodegeneration U.S. Pat. No. 6,348,489 Method of treating traumatic brain injury and other neuronal disorders U.S. Pat. No. 6,420,416 Method of treating epilepsy U.S. Pat. No. 6,423,739 Method for aiding cerebral recovery following neurodegeneration US2001/0051653 A1 Method for improving disturbances of activities of daily living after stroke U.S. Pat. No. 6,399,650 Method for improving disturbances of activities of daily living after stroke

WO2003/030900 REMEDIES FOR ATTENTION-DEFICIENT/HYPERREACTIVITY DISORDER

WO2001/076596 MEDICINE FOR TREATING TRAUMATIC BRAIN INJURY AND OTHER NEURONAL DISORDERS

US2004/0192759 A1 Use of nefiracetam for treating neurodegeneration

US2008/0076820 A1 METHOD FOR TREATING NEURODEGENERATION

US2006/0241144 A1 Method for treating apathy syndrome

EP1171123 B1 METHOD FOR TREATING NEURODEGENERATION

WO2001/062246 A1 METHOD FOR TREATING NEURODEGENERATION

WO2006/113937 A2 METHOD FOR TREATING APATHY SYNDROME

WO2006/113937 A3R4METHOD FOR TREATING APATHY SYNDROME

EP1420782 B1 USE OF NEFIRACETAM FOR TREATING POST-STROKE NEURODEGENERATION

WO2003/018005 A1 Use of nefiracetam for treating neurodegeneration

In one embodiment, the Active is formulated for oral administration and contains between 1 and 50 mg of active. Inactive ingredients include lactose monohydrate, microcrystalline cellulose, pregelatinized starch, croscarmellose sodium, magnesium stearate, polyethylene glycol, polysorbate 80, and titanium dioxide. Alternatively, the inactive ingredients may include colloidal silicon dioxide, crospovidone, hypromellose, lactose monohydrate, magnesium stearate, polyethylene glycol, polysorbate 80, povidone, pregelatinized starch, and titanium dioxide.

In this specification, the term "combination therapy" should be taken to mean that the two therapies (immune mediated therapy and Active-mediated remyelination therapy) are carried out at the same time on the mammal. Thus, the two pharmaceutically-active agents (for example an immune mediated therapeutic such a TYSABRI and an Active such as NEFIRACETAM) may co-administered to an individual, in the form of a single formulation, be it a solid or liquid form, or may be provided as physically separate drugs that are co-administered to the individual, or they may be administered at staggered intervals.

In this specification, the term "pharmaceutical composition" should be taken to mean compositions comprising a therapeutically effective amount of an Active, and immunosuppressant (as defined above) and a pharmaceutically acceptable carrier or diluent. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the 2-oxypyrollidone compound is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, water, dried skim milk, glycerol, and propylene glycol.

The composition, if desired, can also contain minor amounts of wetting or emulsifying agents, or pH buffering agents. These compositions can take the form of solutions, suspensions, emulsion, tablets, pills, capsules, powders, and sustained-release formulations The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the patient.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to, ease pain at the, site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In a preferred embodiment of the invention, the mammal is a human, typically a human suffering from a disease or condition characterised by demyelination of CNS or PNS neuronal cells (i.e. a demyelination disease) such as MS.

BRIEF DESCRIPTION OF THE FIGURES

FIG. 1: Accelerated repair of LPC-induced demyelination in hippocampal organotypic slice culture is a property of racetams in general. Panel A: Representative images showing the persisting decrease in myelin basic protein (MBP; green) in LPC-treated slices compared to control 24 h post-LPC treatment. Nefiracetam, piracetam, aniracetam and levetiracetam all restored MBP expression to control levels or above. Panel B: Quantification of the effect of LPC on MBP expression in the slice culture model and the ability of racetams to restore MBP expression to normal. Data are Mean±SEM percent of field of view positive for MBP, 6≤n≤9. * Significantly different (Student's t-test, p<0.05) from preLPC control. † Significantly different (Student's t-test, p<0.05) from saline-treated control.

FIG. 2: Effect of nefiracetam in the EAE animal model of multiple Sclerosis. Panel A: Study design. Panel B shows the magnitude and timing of clinical symptoms in the EAE model in saline-treated controls and animals treated with nefiracetam from day of inoculation with MBP. Data are Mean±SEM clinical score, n=5. No significant difference was seen.

FIG. 3: Effect of nefiracetam in the EAE animal model of multiple Sclerosis. Panel A: Study design. Panel B shows the magnitude and timing of clinical symptoms in the EAE model in saline-treated controls and animals treated with increasing doses of nefiracetam (9, 15 and 30 mg/kg) from onset of clinical symptoms. Data are Mean±SEM clinical score, n=5. No significant differences were seen.

FIG. 4: Nefiracetam accelerates myelin repair in the cuprizone animal model. Panel A: Study design. Panel B: Representative images showing decreased myelination (dark staining) in the corpus callosum of the adult C57BL/6 mice following 6 weeks on a cuprizone (0.2% wt/wt) diet. Panel C: Quantification of the effect of cuprizone on myelin expression and its recovery 1, 3 and 7 days following return to normal diet. Nefiracetam treatment (30 mg/kg/day) completely restored myelin levels to normal at the 1 day timepoint. Data are Mean±SEM myelin density in arbitrary units, 7≤n≤10

DETAILED DESCRIPTION OF THE INVENTION

The present invention is based on the use of 2-oxopyrolidine compounds ("Active"), especially NEFIRACETAM, as a non-immunomodulatory treatment for demyelinating diseases, especially MS, in which the Active acts to maintain the integrity of myelination. This therapeutic approach is distinct from all the disease modifying drugs currently used in the treatment of MS, and is also applicable for non-autoimmune demyelinating diseases, such as Charcot Marie Tooth type 1 (CMT1). NEFIRACETAM, a member of the racetam family of nootropic drugs, is primarily known for its ability to enhance cognitive function, believed to be due to its modulation of cholinergic nicotinic and glutamatergic NMDA receptors (Narahashi et al, 2004). Clinical studies have already shown that nefiracetam is well tolerated and readily orally administered in humans (Robinson et al, 2009), making it an attractive prospect for application in previously untargeted patient cohorts.

EXPERIMENTAL

Experimental Autoimmune Encephalomyelitis:

A total of 20 female Lewis rats (180-200 g) susceptible to develop experimental autoimmune encephalomyelitis (EAE) were used in this study. Animals were maintained with food and water ad libitum in a 12 h light/dark cycle throughout the study. Under isoflurane anaesthesia each rat received 100 µl of an emulsion containing 50 μg of guinea pig MBP, incomplete Freud's adjuvant and 0.2 mg of *Mycobacterium tuberculosis* H37 Ra, via subcutaneous injection at the base of the tail. Beginning at 7 days post EAE induction, animals received daily intra-peritoneal injections of 9 mg/kg, 15 mg/kg, 30 mg/kg nefiracetam or vehicle only (n=5 per group) until termination of the study. Animals were weighed and assessed for clinical symptoms twice daily by an observer blinded to the treatment. Clinical scores of symptoms were assigned based on the following criteria: 0.5=distal tail limp; 1.0=whole tail limp; 1.5=whole tail limp with slight gait disruption; 2.0=hind limb weakness (waddling gait or one dragging leg); 2.5=hind limb weakness (one dragging leg with some loss of motile function in other leg); 3.0=hind limb paralysis (both legs dragging); 3.5=hindlimb paralysis with some forelimb weakness; 4.0=hind limb and front limb paralysis.

Cuprizone:

Demyelination was induced by feeding 12-14 week old C57B1/6 mice a diet containing 0.2% cuprizone (bis-cyclohexanone oxaldihydrazone) mixed into food pellets. This diet was maintained ad libitum for 6 weeks before returning animals to normal chow (T=0) in order to study remyelination. Control animals received control chow throughout the study. Commencing from 5 days before the return to control chow (T=−5 days), animals received daily intra-peritoneal injections of 30 mg/kg nefiracetam or vehicle only until the end of the study. At different time points, (T=1 day, T=3 days, T=7 days) animals were sacrificed, brains were snap frozen in Optimal Cutting Temperature (OTC) Compound and stored. Coronal frozen sections, 20 μm thick, were cut using a cryostat at approximately −1.8 mm from bregma. Sections were fixed in 70% ethanol, defatted in 50% chloroform/50% ethanol, rehydrated, and then myelin was stained with luxol fast blue. The degree of myelination in the corpus callosum was assessed based on the intensity of the luxol fast blue staining Organotypic Hippocampal Culture.

Organotypic cultures of rat hippocampus were generated from 400 μm slices of hippocampus from 9 day old Wistar rats using the interface method of Stoppini L, Buchs P A, Muller D. (1991) Neurosci Methods. 37:173-82. Slices were maintained in normal organotypic medium for 10 days, at which point demyelination was induced by exposing the cultures to 250 μg/ml lysophosphatidylcholine (LPC) in the medium for 18 hours. After the LPC exposure, slices were returned to LPC free medium containing either 10 μm nefiracetam, 10 μm piracetam, 10 μm levetiracetam, 10 μm aniracetam, or no drug. After a further 24 hours, the cultures were fixed in 4% paraformaldehyde and immunofluorescently labelled for myelin basic protein (MBP) using the method described by Gogolla N, Galimberti I, DePaola V, Caroni P. (2006) Nat. Protoc. 1:2452-6. Labelled MBP in the cultures was imaged by confocal microscopy, and the degree of myelination was compared to time matched cultures that had not undergone LPC exposure.

EAE Study to Show Racetam-Mediated Relief of Visual, Sensory and Motor Symptoms Associated with MS.

The EAE studies with the Lewis rat strain model an acute MS relapse. To better understand the capacity of racetams to alleviate motor, sensory and visual symptoms of MS that are due to the demyelination the mouse model of EAE is employed with the C57BL/6 strain as in this model there is poor natural recovery and symptoms persist due to the demyelination (Gatson et al., 2010 J. Neuroimmunology). A total of 40 female mice are used in this study. Mice are maintained with food and water ad libitum in a 12 h light/dark cycle throughout the study. Under isoflurane anaesthesia each mouse receives an emulsion containing of guinea pig MBP, incomplete Freud's adjuvant and 0.2 mg of *Mycobacterium tuberculosis* H37 Ra, via subcutaneous injection at the base of the tail. Beginning at 7 days post-EAE induction, animals receive daily intra-peritoneal injections of 9 mg/kg, 15 mg/kg, 30 mg/kg nefiracetam or vehicle only (n=10 per group) until termination of the study. Animals are weighed and assessed for clinical symptoms twice daily by an observer blinded to the treatment. Clinical scores of symptoms are assigned based on the following criteria: 0.5=distal tail limp; 1.0=whole tail limp; 1.5=whole tail limp with slight gait disruption; 2.0=hind limb weakness (waddling gait or one dragging leg); 2.5=hind limb weakness (one dragging leg with some loss of motile function in other leg); 3.0=hind limb paralysis (both legs dragging); 3.5=hindlimb paralysis with some forelimb weakness; 4.0=hind limb and front limb paralysis. Reduction in these clinical scores by racetam treatment demonstrates effective treatment of motor symptoms associated with MS. In addition to the above evaluation, these mice are assessed for a normal electroretinogram (ERG) and optic nerve activity by the methods described in Palfi et al. (2010 Hum Gene Ther. 21:311) to show a beneficial effect of racetam treatment on the visual/sensory symptoms seen in MS.

Efficacy of Nefiracetam Treatment in the Animal Model of CMT1A.

The effectiveness of the racetam nefiracetam in improving motor skills and neuromuscular function is tested in a mouse model of CMT1A. The approach used in the curcumin study of Khajavi et al (2007) is followed; using the same animal model and similar behavioural evaluation. However, unlike Khajavi et al (2007), treatment with nefiracetam is started after the onset of neuromuscular deficits. The alternative strategy, beginning treatment early in life, has a greater potential to produce positive therapeutic effects, because there is no dependence in that case on recovery occurring in the system. However, in most cases of human CMT, there is no opportunity to begin treatment before the onset of symptoms; any effective treatment will probably have to alleviate existing symptoms, and reverse or compensate for existing damage. Therefore, this in vivo study is designed not only to model the disease, but the disease at the point where intervention is most likely to occur.

A sample size of 20 animals was used by Khajavi et al (2007) to demonstrate the effectiveness of curcumin in ameliorating the effects of the PMP22 trembler-J mutation on motor control and sciatic nerve structure and function, and was sufficient to detect significant therapeutic effects of treatment, and the same model species and sample size is employed. All experiments are carried out in four treatment groups, 20 mice/group. The first two groups, one of wild type mice, and one of trembler-J mice, each receive 15 mg/kg/day intraperitoneal nefiracetam, while the second two groups (again one wild type and one trembler-J) receive intraperitoneal vehicle daily. Treatment commences in animals at 8 weeks old, i.e. after the emergence of the motor dysfunction of the disease phenotype. Treatment is administered for a period of thirty days, and behavioural assessment carried out during two windows; mid-treatment (days 13-15) and at end of treatment (days 28-30). Behavioural assessment of motor coordination and balance is carried out in all animals using standard rotarod (ENV-575MA, Med Associates) analysis, as used previously to test for therapeutic effects on motor deficits in the trembler-J mice (Khajavi et al, 2007). The rotarod test involves placing the animal on an elevated rod rotating at increasing speed, with time spent on the rod used as an indicator of motor performance. Additionally, during behavioural evaluation windows animals are observed in an open field arena to assess basic locomotor behaviour. The arena consists of a white box 55 cm wide, 55 cm long and 45 cm high. Animals are placed into the box, facing the corner, allowed to explore for a 5 minute period, and tracked using a computerised tracking system (Ethovision 3.1, Noldus) to record the distance moved during the testing period. This observation is used to ensure nefiracetam does not cause a generalized increase in locomotor activity which would affect the interpretation of the rotarod experimental observations.

After 30 days of nefiracetam or vehicle administration and behavioural monitoring, animals are sacrificed, and the sciatic nerves dissected bilaterally. In each animal, one of each pair of nerves is used to assess nerve conduction. Isolated nerves are electrically stimulated at the spinal end, and the evoked compound action potential measured distally. The neurogram compound action potential is assessed to establish the effect of nefiracetam on the changes in amplitude and conduction velocity in the trembler-J mice relative to wild type. The contralateral sciatic nerve is analysed for changes in myelin and axonal structure. Nerves are fixed, immunofluorescently labelled for markers of myelin (MBP) and axons (neurofilament-H), imaged using confocal microscopy, and analysed to assess the degree of cellular dysfunction in each group. Immunofluorescence images are analysed on an axon-by-axon basis using customised automated image analysis software we used previously (O'Sullivan et al, 2010). Parameters to be measured are axon diameter, myelin thickness and number of myelinated axons.

Using the same animals for behavioural, neurophysiological and structural assessment allows for analysis of correlation between the three measured parameters in each animal, as well as reducing the numbers of animals and procedures needed carry out the investigation.

The invention is not limited to the embodiments hereinbefore described, which may be varied in construction, detail and process step without departing from the spirit of the invention.

The invention claimed is:

1. A method of treatment of demyelination as an underlying cause of the disease of multiple sclerosis (MS) in a mammal, the method comprising promoting remyelination of myelination of axonal cells by administering to the mammal a 2-oxopyrrolidine compound having a general formula I:

wherein R=R'=H, and R"=CH$_2$CONH-(2,6CH$_3$)C$_6$H$_3$ or a pharmaceutically acceptable salt thereof.

2. The method of Claim 1 in which the MS is selected from primary progressive MS, secondary progressive MS, relapse remitting MS, and progressive relapsing MS.

3. The method of claim 1 for treating an acute relapse of MS wherein a clinically effective amount of the 2-oxopyrrolidine compound is administered to the mammal upon relapse of MS.

4. A method as claimed in claim 1 in which an immune mediated therapeutic is also administered to the mammal.

* * * * *